United States Patent
Matthias et al.

(10) Patent No.: US 10,571,466 B2
(45) Date of Patent: Feb. 25, 2020

(54) METHOD FOR PRESYMPTOMATIC DIAGNOSIS OF COELIAC DISEASE AND GLUTEN SENSITIVITY

(71) Applicant: Aesku.Diagnostics GmbH & Co. KG, Wendelsheim (DE)

(72) Inventors: Torsten Matthias, Wendelsheim (DE); Sasha Pfeiffer, Bad Kreuznach (DE); Kai Prager, Bad Kreuznach (DE); Christian Meesters, Heidesheim am Rhein (DE); Patricia Jeremias, Woellstein (DE)

(73) Assignee: Aeneas GmbH & Co. KG, Wendelsheim (DE)

( * ) Notice: Subject to any disclaimer, the term of this patent is extended or adjusted under 35 U.S.C. 154(b) by 525 days.

(21) Appl. No.: 14/395,353

(22) PCT Filed: Apr. 17, 2013

(86) PCT No.: PCT/EP2013/001140
§ 371 (c)(1),
(2) Date: Oct. 17, 2014

(87) PCT Pub. No.: WO2013/156156
PCT Pub. Date: Oct. 24, 2013

(65) Prior Publication Data
US 2015/0110818 A1    Apr. 23, 2015

(30) Foreign Application Priority Data

Apr. 17, 2012  (DE) .................. 10 2012 007 508
Apr. 17, 2012  (DE) .................. 10 2012 007 510

(51) Int. Cl.
| | |
|---|---|
| A61K 39/00 | (2006.01) |
| A61K 39/05 | (2006.01) |
| A61K 39/35 | (2006.01) |
| C12Q 1/52 | (2006.01) |
| G01N 33/564 | (2006.01) |
| G01N 33/68 | (2006.01) |

(52) U.S. Cl.
CPC .......... *G01N 33/564* (2013.01); *A61K 39/05* (2013.01); *A61K 39/35* (2013.01); *A61K 2039/55* (2013.01); *G01N 2333/91188* (2013.01); *G01N 2800/06* (2013.01)

(58) Field of Classification Search
None
See application file for complete search history.

(56) References Cited

U.S. PATENT DOCUMENTS 6,703,208 B1   3/2004   Rajadhyaksha et al.

FOREIGN PATENT DOCUMENTS

| | | |
|---|---|---|
| DE | 19814860 A1 | 10/1999 |
| DE | 69535037 T2 | 12/2006 |
| WO | 2007020291 A1 | 2/2007 |
| WO | 2008053310 A2 | 5/2008 |

OTHER PUBLICATIONS

Ngo et al. 'Computational Complexity, Protein Structure Prediction, and the Levinthal Paradox'. The Protein Folding Problem and Tertiary Structure Prediction. Ed. K. Merz and S. Le Grand. Boston: Birkhauser, 1994.491-495.*
Skolnick et al. 'From genes to protein structure and function: novel applications of computational approaches in the genomic era.' Trends in Biotech. 18:34-39, 2000.*
Attwood et al. 'The Babel of Bioinformatics.' Science. 290(5491):471-473.*
Blumenthal et al. 'Definition of an Allergen.' Allergens and Allergen Immunotherapy. Ed. R Lockey, S. Bukantz and J. Bousquet. New York: Marcel Decker, 2004.37-50.*
Fleckenstein et al. 'Molecular Characterization of Covalent Complexes between Tissue Transglutaminase and Gliadin Peptides*.' J. Biol. Chem. 279(17):17607-17616, 2004.*
Gianfrani et al. Transamidation of Wheat Flour Inhibits the Response to Gliadin of Intestinal T Cells in Celiac Disease. Gastroenterol. 133:780-789, 2007.*
Matthias et al. Diagnostic Challenges in Celiac Disease and the Role of the Tissue Transglutaminase—Neo-Epitope. Clin. Rev. Allerg. Immunol. 38(2-3):298-301, 2010.*
Written Opinion of the International Searching Authority for PCT/EP2013/001140 dated Sep. 3, 2013 (Form PCT/ISA/237).
International Search Report for PCT/EP2013/001140 dated Sep. 3, 2013 (Forms PCT/ISA/220, PCT/ISA/210).
Skovbjerg H., et al., "Deamidation and cross-linking of gliadin peptides by transglutaminases and the realtion to celiac disease" Biochimica et Biophysica Acta, Molecular Basis of Disease Amsterdam, NL, Bd. 1690, Nr. 3, Nov. 5, 2014, pp. 220-230.
Skovbjerg H., et al. "Gliadin is a Good Substrate of Several Transglutaminases: Possible Implication in the Pathogenesis of Coeliac Disease" Scandinavian Journal of Gastroenterology, Bd. 37, Nr. &, Jul. 2002, pp. 812-817.
Dekking, et al., "Microbial transglutaminases generate T cell stimulatory epitopes involved in celiac disease", Journal of Cereal Science, Academic Press Ltd., 47 (2008) pp. 339-346.
Bizzaro, N., et al., "Cutting-Edge Issues in Celiac Disease and in Gluten Intolerance" Clinical Reviews in Allergy & Immunology, Humana Press Inc., New York, (2012) 42:279-287.

(Continued)

*Primary Examiner* — Nora M Rooney
(74) *Attorney, Agent, or Firm* — Buchanan Ingersoll & Rooney PC

(57) ABSTRACT

The invention relates to the use of an immunologically reactive microbial transglutaminase or its immunologically reactive parts or analogues, which are present in a complex with gliadin or its immunologically reactive parts or analogues, for the diagnosis and/or therapy control of coeliac disease or sprue as well as gluten sensitivity, and a kit for determining the diagnosis and/or therapy control of coeliac disease or sprue as well as of gluten sensitivity, by means of the previously mentioned complex.

9 Claims, 10 Drawing Sheets

Specification includes a Sequence Listing.

(56) References Cited

OTHER PUBLICATIONS

International Preliminary Report on Patentability for PCT/EP2013/001140 dated Oct. 30, 2014 (Form PCT/ISA/373) (English Translation).
International Preliminary Report on Patentability for PCT/EP2013/001140 dated Oct. 30, 2014 (Form PCT/ISA/373) (German Translation).
Fitch, W.M., Homology: a personal view on some of the problems; Trends in Genetics, vol. 16, No. 5, 2000, pp. 227-231.
German Office Action dated Jan. 28, 2013 for Application No. 10 2012 007 508.1.
German Office Action dated Jan. 28, 2013 for Application No. 10 2012 007 510.3.
Matthias, T. et al.; The Industrial Food Additive, Microbial Transglutaminase, Mimics Tissue Transglutaminase and is Immunogenic in Celiac Disease Patients, Autoimmunity Reviews, 2016, pp. 1111-1119, vol. 15, Elsevier B.V.
Jeremias, P et al., The Industrial Food Additive Microbial Transglutaminase is Immunogenic in Children with Celiac Disease, Presented on the 10th International Congress on Autoimmunity, Apr. 6-10, 2016, Aesku.Kipp Institute GmbH & Co. KG, Wendelsheim, Germany.
Lerner, A. et al., Possible Association Between Celiac Disease and Bacterial Transglutaminase in Food Processing: A Hypothesis, Nutrition Reviews Advance Access, Jun. 16, 2015, pp. 1-9.
Martin Griffin et al., "Transglutaminases: Nature's biological glues," Biochem. J. (2002) 368, 377-396.
P.D. Howdle et al., "Review of methods for measuring gliadins in food," Gut, 1990, 31, 712-713.

* cited by examiner

FIG. 1A

Upper Sequence MTG (SEQ ID NO:1); Lower Sequence TG2 (SEQ ID NO:3)

```
########################################
# Program: stretcher
# Rundate: Wed 15 Feb 2012 12:55:20
# Commandline: stretcher
#    -auto
#    -stdout
#    -asequence emboss_stretcher-I20120215-125459-0781-25279230-oy.asequence
#    -bsequence emboss_stretcher-I20120215-125459-0781-25279230-oy.bsequence
#    -datafile EBLOSUM62
#    -gapopen 12
#    -gapextend 2
#    -aformat3 pair
#    -sprotein1
#    -sprotein2
# Align_format: pair
# Report_file: stdout
########################################

#=======================================

# Aligned_sequences: 2
# 1: EMBOSS_001
# 2: EMBOSS_001
# Matrix: EBLOSUM62
# Gap_penalty: 12
# Extend_penalty: 2

# Length: 692
# Identity:      99/692 (14.3%)
# Similarity:   163/692 (23.6%)
# Gaps:         287/692 (41.5%)
# Score: -522

#=======================================

EMBOSS_001         1 MSQRGRTLVFAALGAVMCTTALMPSAGAATGSGSGSGTGEE--KRSYAET       48
                     |::.  ||.........:.|........................|:.  ...:|.
EMBOSS_001         1 MAEE----LVLERCDLELETNGRDHHTADLCREKLVVRRGQPFWLTLHFEG      47

EMBOSS_001        49 HRLTADDVDDINALNESAPAASS-AGPSFRAPDSDE---------------      83
                     ....|. ||.:......:|].|. ||...|.|..|.
EMBOSS_001        48 RNYEAS-VDSLTFSVVTGPAPSQEAGTKARFPLRDAVEEGDWTATVVDQQ      96

EMBOSS_001        84 ------RVTPPAEP----LDRMPDPYRPSYGRAETIVNNYI---RKW---Q     118
                           ::|.||.. |.|:.........|...:..::.:|  ..|  .
EMBOSS_001        97 DCTLSLQLTTPANAPIGLYRLSLEASTGYQGSSFVLGHFILLFNAWCPAD     146

EMBOSS_001       119 QVYSHRDGRKQQMTEEQREWLSYGCV----GVTWVNSGQYPTNRLAFAFF     164
                     .||...:|..:|:.....|:..:.|..        ,:.| |.||:.....|......
EMBOSS_001       147 AVYLDSEEERQEYVLTQQGFIYQGSAKFIKNIPW-NFGQFEDGILDICLI     195

EMBOSS_001       165 DEDKYKNELKN-GRPRSGETRAEFEGRVAKD-------------------     194
                     ..|......||| ||...|..:.....:.|||...
EMBOSS_001       196 LLDVNPKFLKNAGRDCSRRSSPVYVGRVVSGMVNCNDDQGVLLGRWDNNY     245

EMBOSS_001       195 -----------SFDEAK------GFQRAR---------DVASVMNKAL----     216
                                |.|...:     |.|.|..:           .||...:.:.|
EMBOSS_001       246 GDGVSPMSWIGSVDILRRWKNHGCQRVKYGQCWVFAAVACTVLRCLGIPT     295

EMBOSS_001       217 ------ENAHDEGA------YLDNLKKELANGNDAL------------RNE     243
                           .:||||.:      |..|...|:            ...
EMBOSS_001       296 RVVTNYNSAHDQNSNLLIEYFRNEFGEIQGDKSEMIWNFHCWVESWMTRP     345
```

FIG. 1B

```
EMBOSS_001   244  DARSPF---YSALRNTPSFKDRNGGNHDPSKMKAVI-------YSKHFWSG   284
                  |.:..:   :.||..||..|..........|...:: :.   |...|...
EMBOSS_001   346  DLQPGYEGWQALDPTPQEKSEGTYCCGPVPVRAIKEGDLSTKYDAPFVFA   395

EMBOSS_001   285  QDRSGSSDKRKYGDPEAFRPDRGTGLV---------------DMSRDRNI   319
                  :..:...|..:..|....:....:.:|                |::.....
EMBOSS_001   396  EVNADVVDWIQQDDGSVHKSINRSLIVGLKISTKSVGRDEREDITHTYKY   445

EMBOSS_001   320  PRSPTSPGESFVNFDY----------GW-----FGAQTEADADKTVWTHG   354
                  |...:...|:|....::         |.    .|........:|..|:.|.
EMBOSS_001   446  PEGSSEEREAFTRANHLNKLAEKEETGMAMRIRVGQSMNMGSDFDVFAHI   495

EMBOSS_001   355  NHYHAP---------------NGSLGA-----------------------MH   368
                  .:..|.                ||.||.                        :.
EMBOSS_001   496  TNNTAEEYVCRLLLCARTVSYNGILGPECGTKYLLNLNLEPFSEKSVPLC   545

EMBOSS_001   369  VYESKFRNWS-----------------DGYSDFDRGAYV--------VTF   393
                  :...|:|:..                  :.|...:|..|:          :..
EMBOSS_001   546  ILYEKYRDCLTESNLIKVRALLVEPVINSYLLAERDLYLENPEIKIRILG   595

EMBOSS_001   394  VPKS-----------WNTAP-----------------------------   402
                  .||.           .|..|
EMBOSS_001   596  EPKQKRKLVAEVSLQNPLPVALEGCTFTVEGAGLTEEQKTVEIPDPVEAG   645

EMBOSS_001   403  -----------------------DKVKQ---------GWP           410
                                         ||:|.          |..
EMBOSS_001   646  EEVKVRMDLLPLHMGLHKLVVNFESDKLKAVKGFRNVIIGPA         687
```

FIG. 2A

Upper Sequence MTG (SEQ ID NO:1); Lower Sequence TG2 (SEQ ID NO:3)

```
########################################
# Program: needle
# Rundate: Wed 15 Feb 2012 12:52:01
# Commandline: needle
#    -auto
#    -stdout
#    -asequence emboss_needle-I20120215-125159-0923-93477931-oy.asequence
#    -bsequence emboss_needle-I20120215-125159-0923-93477931-oy.bsequence
#    -datafile EBLOSUM62
#    -gapopen 10.0
#    -gapextend 0.5
#    -endopen 10.0
#    -endextend 0.5
#    -aformat3 pair
#    -sprotein1
#    -sprotein2
# Align_format: pair
# Report_file: stdout

########################################

#=======================================

# Aligned_sequences: 2
# 1: EMBOSS_001
# 2: EMBOSS_001
# Matrix: EBLOSUM62
# Gap_penalty: 10.0
# Extend_penalty: 0.5

# Length: 811
# Identity:      75/811 ( 9.2%)
# Similarity:   124/811 (15.3%)
# Gaps:         525/811 (64.7%)
# Score: 48.0

#=======================================

EMBOSS_001         1 ------------------------------MSQRGR-----TLVFAALGA     15
                                                   :.:||:    ||.|.....
EMBOSS_001         1 MAEELVLERCDLELETNGRDHHTADLCREKLVVRRGQPFWLTLHFEGRNY     50

EMBOSS_001        16 VMCTTALMPS--AGAATGSGSGSGTGEEKRSYAETHRLTADDVDDIN---     60
                     .....:..|   .|.|....:|:......|...|....||..||..:
EMBOSS_001        51 EASVDSLTFSVVTGPAPSQEAGTKARFPLRDAVEEGDWTATVVDQQDCTL    100

EMBOSS_001        61 ALNESAPAASSAGPSFRAPDSDERVTPPAEPLDRMPDPYRPSYGRAETIV    110
                     :|..:.||.:..|                       |.|:........|...:..::
EMBOSS_001       101 SLQLTTPANAPIG----------------------LYRLSLEASTGYQGSSFVL    132

EMBOSS_001       111 NNYI----RKW---QQVYSHRDGRKQQMTEEQREWLSYGCV-----GVTWVN    150
                     .::|    ..|   ..||.......|......||.....     .:.| |
EMBOSS_001       133 GHFILLFNAWCPADAVYLDSEEERQEYVLTQQGFIYQGSAKFIKNIPW-N    181

EMBOSS_001       151 SGQYPTNRLAFAFFDEDKYKNELKN-GRPRSGETRAEFEGRVAKDSFDEA    199
                     .||:....|..........|......|||  ||..|...:..:.|||
EMBOSS_001       182 FGQFEDGILDICLILLDVNPKFLKNAGRDCSRRSSPVYVGRV-------V    224

EMBOSS_001       200 KGFQRARDVASVMNKALENAHDEG----AYLDNLKKELANGNDALRNEDA    245
                     .|......|...|:....:|.::|    :::.::   |.||.
EMBOSS_001       225 SGMVNCNDDQGVLLGRWDNNYGDGVSPMSWIGSV--------DILRR---    263

EMBOSS_001       246 RSPFYSALRNTPSFKDRNGGNHDPSKMKAVIYSKHFWSGQDRSGSSDKRK    295
                                                        |      ::.....:.|
```

FIG. 2B

```
EMBOSS_001   264 --------------------------------W----KNHGCQRVK      273

EMBOSS_001   296 YGDPEAFR-------------PDRGTGLVDMSRDRNIPRSPTSPGESFVNF  333
                 ||....|.             .|..........:.:|:|    .....:.:
EMBOSS_001   274 YGQCWVFAAVACTVLRCLGIPTRVVTNYNSAHDQN--------SNLLIEY   315

EMBOSS_001   334 DYGWFGAQTEADADKTVWTHGNHYHAPNGSLGAMHVYESKFRNWSDGYSD   383
                     .||  :.:.|...:.|                        .|..1.:
EMBOSS_001   316 FRNEFG-EIQGDKSEMIW---------------------NFHCWVE----  339

EMBOSS_001   384 FDRGAYVVTFVPKSWNTAPDKVK--QGWP---------------------  410
                     ||.|.||...  :||.
EMBOSS_001   340 -------------SWMTRPDLQPGYEGWQALDPTPQEKSEGTYCCGPVPV  376

EMBOSS_001   411 --------------------------------------------------  410
EMBOSS_001   377 RAIKEGDLSTKYDAPFVFAEVNADVVDWIQQDDGSVHKSINRSLIVGLKI   426

EMBOSS_001   411 --------------------------------------------------  410
EMBOSS_001   427 STKSVGRDEREDITHTYKYPEGSSEEREAFTRANHLNKLAEKEETGMAMR   476

EMBOSS_001   411 --------------------------------------------------  410
EMBOSS_001   477 IRVGQSMNMGSDFDVFAHITNNTAEEYVCRLLLCARTVSYNGILGPECGT   526

EMBOSS_001   411 --------------------------------------------------  410
EMBOSS_001   527 KYLLNLNLEPFSEKSVPLCILYEKYRDCLTESNLIKVRALLVEPVINSYL   576

EMBOSS_001   411 --------------------------------------------------  410
EMBOSS_001   577 LAERDLYLENPEIKIRILGEPKQKRKLVAEVSLQNPLPVALEGCTFTVEG   626

EMBOSS_001   411 --------------------------------------------------  410
EMBOSS_001   627 AGLTEEQKTVEIPDPVEAGEEVKVRMDLLPLHMGLHKLVVNFESDKLKAV   676

EMBOSS_001   411 ----------   410
EMBOSS_001   677 KGFRNVIIGPA  687
```

METHOD FOR PRESYMPTOMATIC DIAGNOSIS OF COELIAC DISEASE AND GLUTEN SENSITIVITY

CROSS REFERENCE TO RELATED APPLICATIONS

This application is the United States National phase under 35 U.S.C. § 371 of PCT International Patent Application No. PCT/2013/001140, filed on Apr. 17, 2013, and claiming priority to German application no. 102012007510.3, filed on Apr. 17, 2012, and German application no. 102012007508.1, filed on Apr. 17, 2012.

BACKGROUND OF THE INVENTION

Field of the Invention

Embodiments relate to diagnostic testing for coeliac disease, sprue, and/or gluten sensitivity.

Background of the Related Art

Coeliac disease, also known as gluten-sensitive enteropathy or sprue, is a chronic inflammation of the small intestine often associated with extensive destruction of the intestinal epithelial cells, which may result in a malabsorption syndrome and/or associated immunological disorders.

The inflammation, if the corresponding genetic predisposition is present, is activated by a hypersensitivity to gluten, a collective term for the "sticky proteins" present in many cereal types. In wheat, the immunogenic prolamin (the alcohol-soluble fraction) is called gliadin. Homologous prolamins are also known in rye (secalins), barley (hordeins) and oats (avenins). In persons with the appropriate predisposition, these peptide fragments can result in a complex reaction of the intestinal mucosa and of the immune system.

The term gluten also covers gluten derivatives, gliadin or gliadin homologue extracts, non-synthetically or synthetically produced gliadin peptides and chemical derivatives of these known as "gliadin peptide".

Certain gliadin peptides or homologous prolamin peptide fragments are absorbed by antigen-presenting cells, processed and loaded onto HLA molecules or bind directly to HLA molecules, principally to HLA-DQ2 or HLA-DQ8. This binding is reinforced by the deamidation of the amino acid glutamine that is frequently present in the peptide. This deamidation is principally catalysed via the enzyme tissue transglutaminase (tTg), and in particular by tissue transglutaminase 2 (tTg2). In addition the enzyme also catalyses a transamidation, by means of which a cross-linking of the surrounding peptides and proteins is induced. The deamidation of gliadin peptides guarantees high-affinity binding between the gliadin peptide and, for example, HLA-DQ2.

This peptide-HLA complex in turn binds to the CD4+T helper cells, which in turn leads to activation of the inflammatory cytokine cascade. This increases the production of various inflammation-triggering messenger substances, such as interferon-gamma, TNF-alpha, interleukin-6 and interleukin-2.

In the course of the inflammation, various antibodies are formed which target, for example, gliadin itself (gliadin antibodies) or tissue transglutaminase (tTg antibodies). Ultimately the inflammation process ends in the apoptosis of the enterocytes (lining cells of the epithelium of the small intestine), which leads to a more or less pronounced loss of small intestinal villi (villous atrophy). This results in the mucosa of the small intestine no longer being in a position to transfer sufficient nutrients from the intestine to the bloodstream, resulting ultimately in a malabsorption syndrome.

The prevalence (number of sufferers at the time of investigation/number of "studied" individuals) of coeliac disease or endemic sprue is 1:100, more recent studies, however, assume a prevalence of approx. 1:50. All in all, coeliac disease or endemic sprue reaches a frequency of 1% to 3% within the Caucasian population group.

Coeliac disease exhibits two manifestation peaks, one in infancy from approx. 6 to 18 months, one to three months after cereals have been included in the diet and a second peak aged approx. 30 to 40 years.

The most common symptoms of coeliac disease or sprue are chronic diarrhoea, iron deficiency with or without anaemia and osteopenia, cause by the digestive disorder. Failure to thrive can often be observed in affected children. Less common symptoms include chronic fatigue, nervousness, osteoporosis, osteomalacia, anxiety disorders, depression, muscle cramps and secondary lactose intolerance. Furthermore, various concomitant diseases may occur, such as selective IgA deficiency, dermatitis herpetiformis, diabetes Type I and gastrointestinal malignoma.

Diagnosis of coeliac disease or sprue is preferably or usually performed by means of a serological diagnosis and/or by means of histology of biopsies of the small intestine. The serological diagnosis of coeliac disease or sprue is normally tested for the presence of antibodies against a foreign antigen, such as gliadin (anti-gliadin antibodies) or deamidated gliadin peptide (anti-DGP antibodies) and against autoantigens of the endomysium (anti-EMA antibodies), but especially against tissue transglutaminase 2 (anti-tTg2 antibodies) or a complex of tissue transglutaminase and gliadin (anti-tTg/gliadin peptide complex antibodies).

Auto antibodies against endomysial antigens are highly specific and can be demonstrated in over 90% of patients with coeliac disease or with endemic sprue. In this case, an indirect immunofluorescence test on tissue sections from primate oesophagus is used. The anti-endomysium concentrations reflect the histological appearance: the higher the antibody titres are, the more pronounced is the villous atrophy. However, anti-endomysium detection by means of the immunofluorescence technique is fairly costly, as this test requires the user to have a high degree of technical competence, is time consuming and requires relatively rare biological material (primate oesophagus tissue).

From a historical perspective, the detection of antibodies against gliadin offered the first opportunity of identifying coeliac disease or endemic sprue by means of an antibody test procedure. However, anti-gliadin antibodies are not specific enough to detect endemic sprue to a satisfactory extent. The detection sensitivity was improved thanks to the discovery of anti-deamidated gliadin peptide (DGP) antibodies. A further improvement in the diagnosis and clinical monitoring of this disorder was the discovery of anti-tissue transglutaminase antibodies.

When it comes to the serological diagnosis of coeliac disease, the presence of anti-endomysial antibodies is usually detected.

A central aspect of coeliac disease diagnosis was, and to some extent remains, a histological examination of a biopsy of the small intestine, whereby the histopathological spectrum may range from minimum elevation of intraepithelial lymphocytes to complete villous atrophy. The characteristic histopathological elements for the above are: an increase in intraepithelial lymphocytes as well an increase in lymphocytes and plasma cells in the lamina propria, frequently mixed with eosinophils; reduced villi length, deepening of the intestinal crypts; reduced villi: Crypt ratio (normally >4-5:1); increased mitotic cell count; abnormal enterocytes (cuboid rather than cylindrical cells, loss of basal core polarity, loss of the brush border).

The histological grading is usually performed on the basis of the classification proposed by Marsh.

TABLE

Distribution of the Marsh criteria [A. Vècsei et al. 2011, p. 6]

| Type | Crypts | Villi |
|---|---|---|
| 0 | normal | normal |
| 1 | normal | normal |
| 2 | hyperplastic | normal |
| 3a | hyperplastic | slightly truncated |
| 3b | hyperplastic | severely truncated |
| 3c | hyperplastic | totally absent |

On the basis of the diagnosis of symptoms, histological findings and serological findings, as well as genetic and clinical information, coeliac disease or endemic sprue can be assigned to various clinical sub-groups. These range from what is known as "silent sprue", to "latent sprue", and right through to manifest or classic sprue.

An early diagnosis of coeliac disease or endemic sprue is crucial to the progression of the disease. Following reliable and early diagnosis, the disease can be kept in remission through consistent observance of a gluten-free diet and the risks of concomitant and/or secondary illnesses, such as increased malignoma risk, can be prevented.

Therefore continuing to improve diagnostic tests for coeliac disease or endemic sprue is of primary concern. When it comes to a rapid, easy-to-perform, economical test, serological diagnostic procedures appear to be particularly suitable.

For example, EP 0 912 898 B1 teaches an immunological diagnostic procedure for antibodies that target tissue transglutaminase (tTg). In this diagnostic procedure, antibodies against tissue transglutaminase (tTG) from body fluids are demonstrated by means of an immune reaction with tissue transglutaminase, whereby the immune reaction is not performed with a tissue section from animal or human tissue.

Furthermore, test procedures are available which can detect antibodies which target a complex of tissue transglutaminase (tTG) and gliadin peptides. Such test procedures are, for example, offered by the company AESKU.Diagnostics. It has been shown with this test procedure that antibody formation can be proved before all other state-of-the-art tests.

Furthermore, even gluten intolerance or sensitivity is identified, which is not induced by coeliac disease. A distinction should be made between this disease, which is neither an autoimmune disorder or a wheat allergy, and coeliac disease. Both must first be excluded before it can be diagnosed. Furthermore, it must be determined as to whether there is any improvement with a gluten-free diet. No biomarkers have previously been identified for this disorder.

BRIEF SUMMARY OF THE INVENTION

Embodiments may provide a diagnostic test which is able, even prior to the development of symptoms, i.e. presymptomatically, to detect coeliac disease or sprue as well as gluten sensitivity, and hence enables the early diagnosis or therapy control of coeliac disease and sprue or general gluten intolerance and gluten sensitivity.

According to an embodiment of the invention, it was discovered that for the diagnosis and/or therapy control of coeliac disease or sprue and gluten sensitivity at least one functional, immunologically reactive complex of microbial transglutaminase (mTG) or its immunologically reactive parts and gliadin and/or gliadin peptides or their immunologically reactive parts are used instead of tissue transglutaminase (tTG). In the following, the term gliadin is not only understood to refer to gliadin itself but also gliadin peptides and immunologically reactive parts thereof.

BRIEF DESCRIPTION OF THE FIGURES

FIG. 1A and FIG. 1B show a paired alignment of the amino acid sequences of microbial transglutaminase (mTG) from Streptomyces mobaraensis (SEQ ID NO: 1) and from human tissue transglutaminase 2 (TG2) (SEQ ID NO: 3) using the "stretcher" algorithm. The sequence comparison was performed by means of the pairwise alignment tool EMBOSS (from EMBL-EBI) that is freely available on the Internet.

FIG. 2A and FIG. 2B show a paired alignment of the amino acid sequences of microbial transglutaminase (mTG) from *Streptomyces mobaraensis* and from human tissue transglutaminase 2 (TG2) using the "needle" algorithm. The sequence comparison was performed by means of the pairwise alignment tool EMBOSS (from EMBL-EBI) that is freely available on the internet.

The individual components of the measurement can be obtained from the diagram legend.

Figure 10:
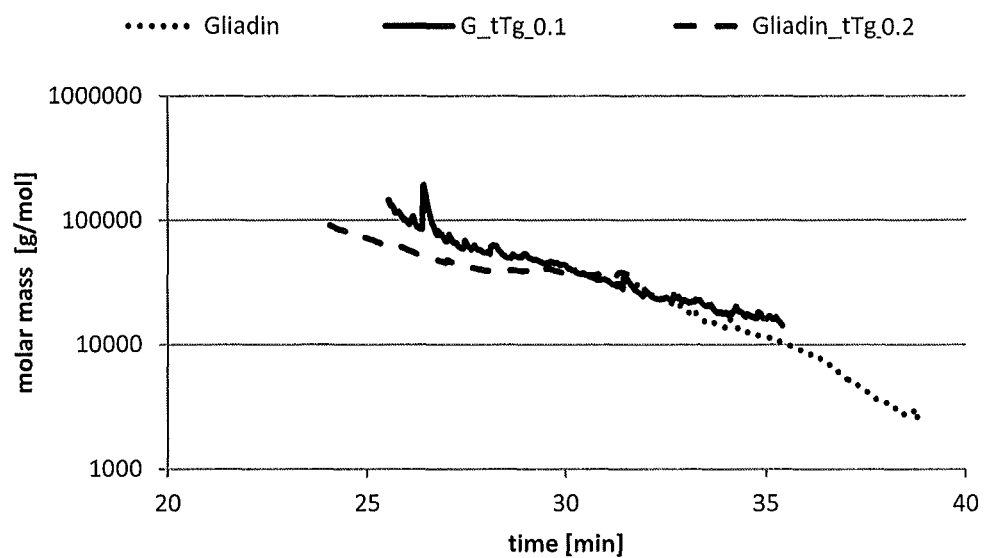

FIG. 10 shows the results, in the form of a diagram, of a measurement via SEC-MALS for the formation of complexes of gliadin and tissue transglutaminase, whereby the molar mass in g/mol is presented in relation to time. The individual components of the measurement can be obtained from the diagram legend.

Figure 11:
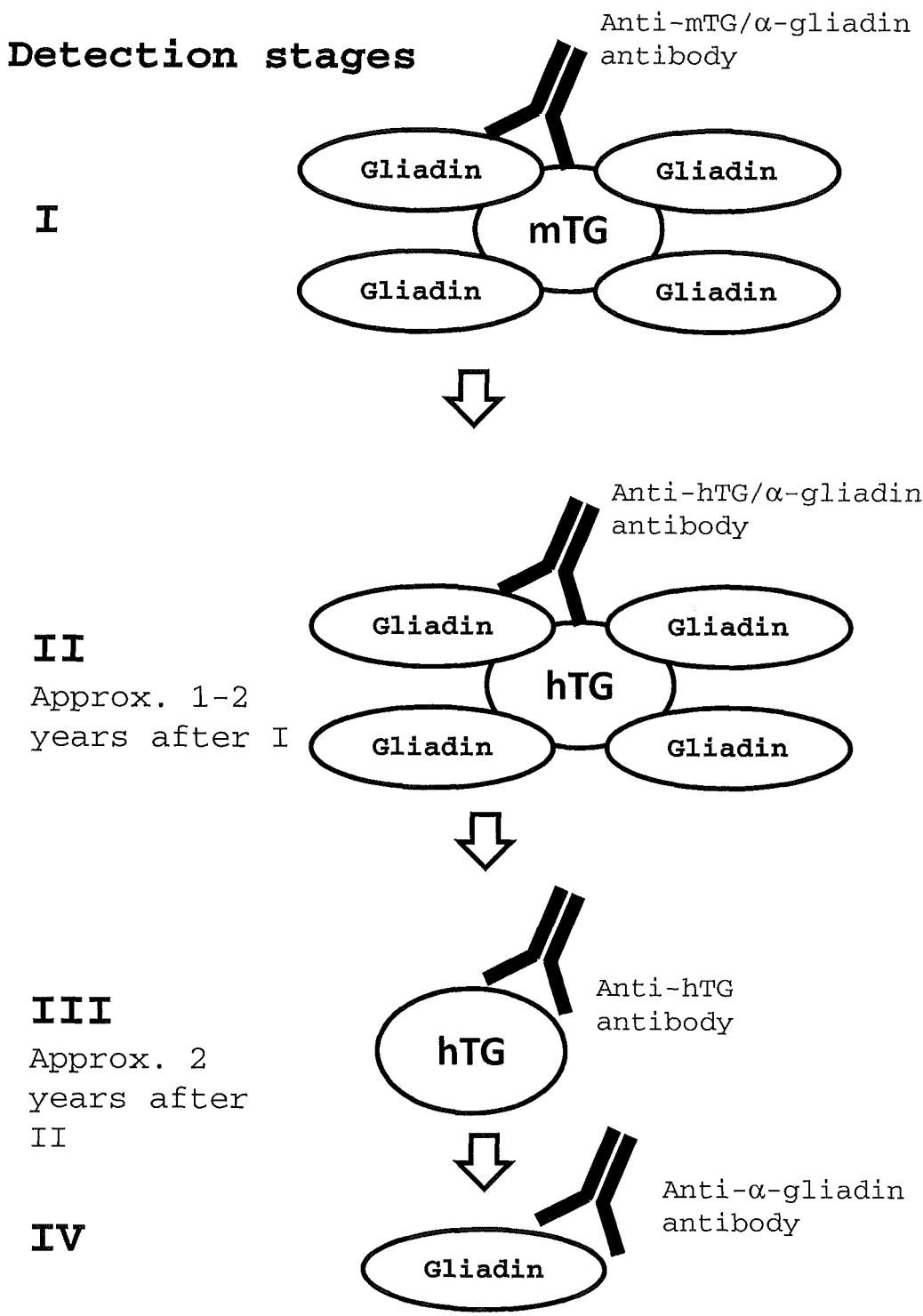

FIG. 11 shows a schematic sub-division of various detection stages for coeliac disease or sprue. The basis for this is the time lapse in (initial) occurrence of the various diagnostic antibodies.

Figure 12:
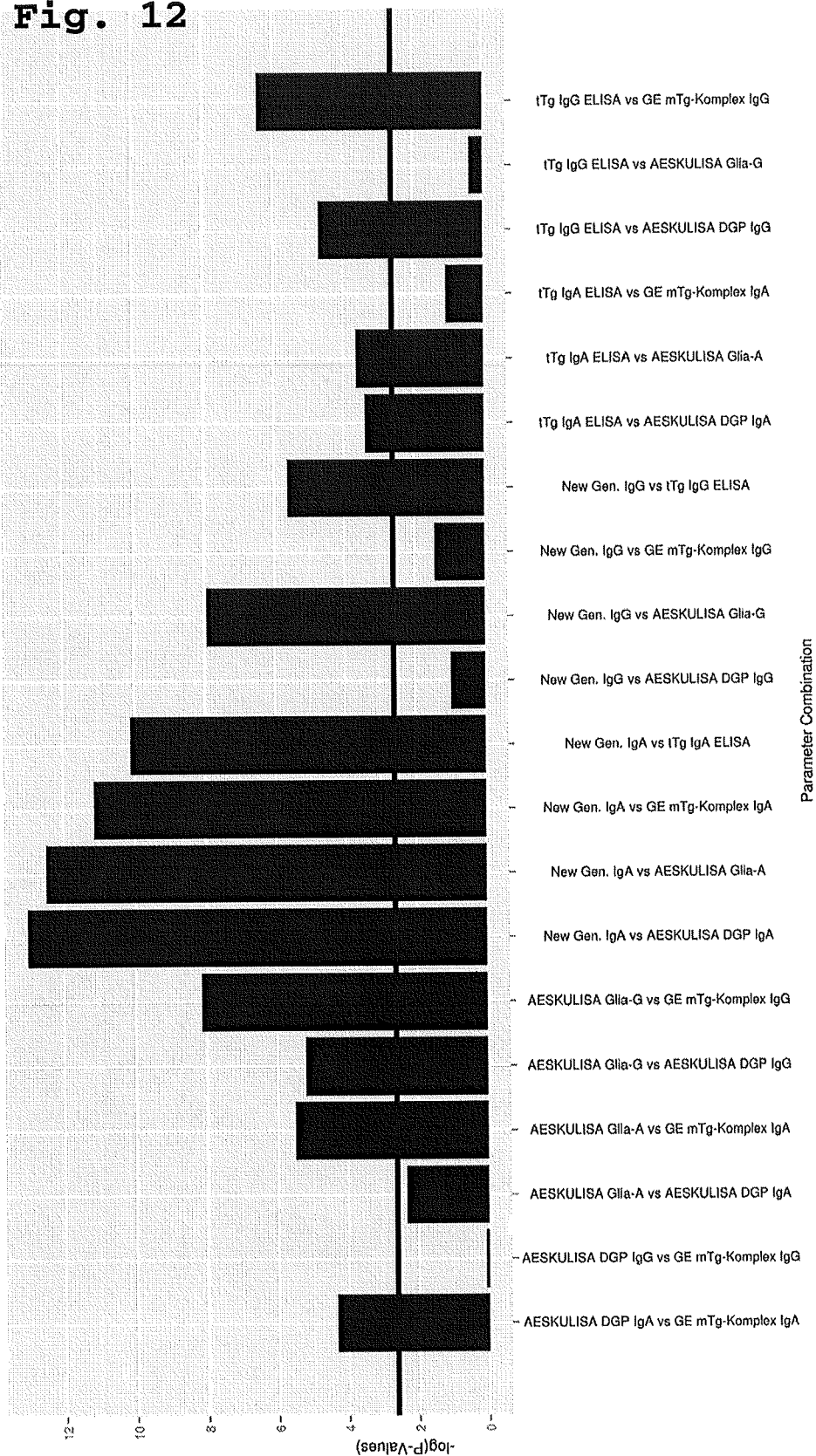

FIG. 12 shows: −log(P values) of the Wilcoxon-Mann-Whitney tests for verifying the presumed sequence of antibody appearance.

DETAILED DESCRIPTION OF THE INVENTION

Surprisingly, it was discovered that even at an early stage of the previously named diseases, antibodies can be identified which bind to a complex that is formed of microbial transglutaminase and gliadin. This is all the more surprising since microbial transglutaminase has a completely different sequence from human tissue transglutaminase (tTg).

As with the function of tissue transglutaminase, it is also assumed in the generation of the complex used in accordance with the invention that the ratio of deamidation to transamidation is 4:1 and the complex used in accordance with the invention does not necessarily present a molecular species covalently complexed to transglutaminase. The complex is preferably formed by incubation of gliadin peptides and microbial transglutaminase. The individual component mTg does not exhibit any immunological activity in human samples, gliadin peptides are known antigens according to the latest technology and therefore exhibit immunological activity in human patient samples. The immunological activity is, however, significantly higher after complex formation between gliadin peptides and mTg than the sum of the individual components.

As with the complex of tTg2 and gliadin peptides, when the complex is used in accordance with the invention it is also assumed that the distribution of cross-linked gliadin peptides and the enzyme occurs on a stochastic basis, which is confirmed by the light scatter measurements. These complexes contain microbial transglutaminase and display immunological activity that is suitable for intercepting the epitopes from tTg2 with gliadin peptides in competitive assays.

Figure 5:
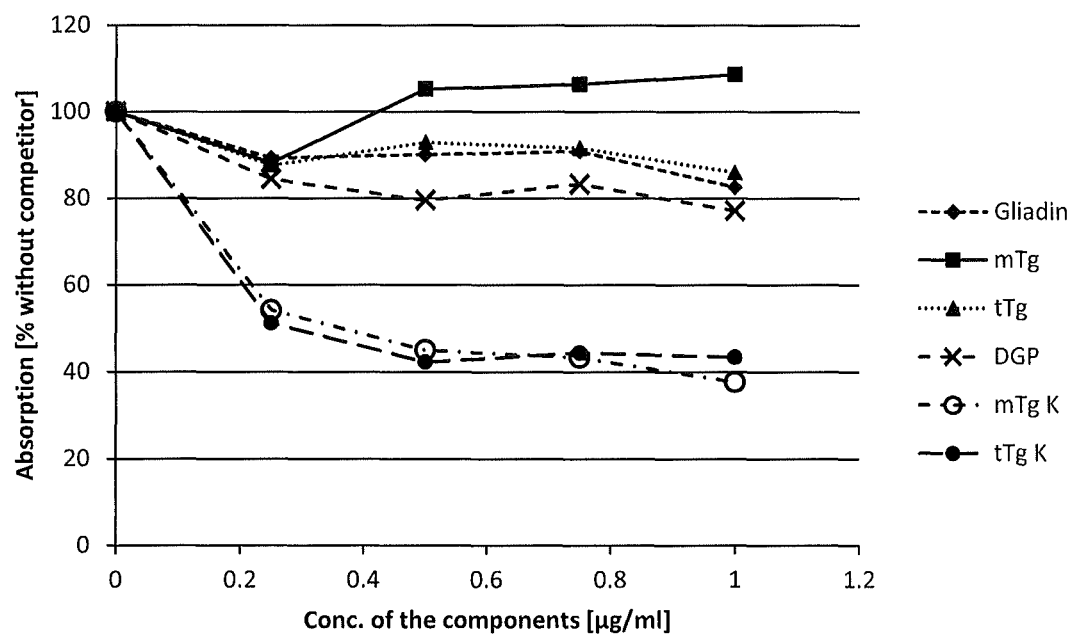
FIG. 5 shows the results of a competitive assay for serum 1011 (IgG) in the form of a diagram, whereby the absorption is presented in relation to the concentration of the competitors. The individual competitors can be obtained from the diagram legend.

This is demonstrated by competitive assays, which were performed with various patient serums (see FIG. 5).

Embodiments relate to antibodies which bind to the complex used in accordance with the invention consisting of microbial transglutaminase and gliadin peptides or to the immunologically active parts of this complex. Antibodies in terms of this invention include both polyclonal and/or monoclonal antibodies and/or aptamers. An antibody is understood to be a protein which presents one or more specific antigen-binding sites. The expert is, without unreasonable effort, to generate an antibody which specifically binds to the complex used in accordance with the invention consisting of microbial transglutaminase and gliadin peptides or to immunologically active parts of this complex. The corresponding techniques and approaches are familiar to the expert from everyday laboratory practice. The antibodies in accordance with the invention may, for example, also be generated by isolating and cleaning the antibodies present in the serum of coeliac disease or sprue patients or gluten-sensitive patients by means of a complex used in accordance with the invention and hence made accessible. Without being bound, it is presumed that the antibodies bind to a neoepitope in the vicinity of the active centre of the enzyme mTgase. In addition, the complex used in accordance with the invention can, for example, be coupled to a substrate, the loaded substrate is then brought into contact with coeliac disease or sprue patient serum. Non-specifically bound components of the serum are removed and the antibodies specifically bound to the complex used in accordance with the invention are then eluted.

Embodiments relate to the use of the complex of microbial transglutaminase or gliadin or their immunologically active parts for in vitro detection of antibodies that bind to this complex. Use in accordance with this invention is characterised by:

1. A complex used in accordance with the invention being brought into contact with a sample in vitro; and
2. Antibodies being detected that are bound to the complex used in accordance with the invention.

For the purposes of this invention, the term "in vitro" is understood to be any environment that is not within a complete organism, for example a human or animal body.

Sample is understood to be a composition that is to be investigated. Preferably, the sample is a biological or medical material, i.e. material that is extracted from an organism or from components of an organism or cells. Before it is used as a sample in the procedure in accordance with the invention, the material may be subjected to further processing steps, for example in order to convert the material to a state in which it is especially suitable for use as a sample for the procedure. Particular preference is given to samples based on material that is obtained from a body fluid or that consists of a body fluid. Preferred body fluids are blood, plasma, serum, lymph fluid, synovial fluid, urine, stool, interstitial fluid, saliva, sweat, spinal fluid, breast milk and/or tear fluid. Particular preference is given to body fluids in which antibodies are to be found in high concentrations.

When used in accordance with the invention, a complex used in accordance with the invention is brought into contact in vitro with a sample to be investigated. The step of bringing into contact is designed to ensure that any antibodies contained in the sample have the possibility to bind to an epitope of the complex used in accordance with the invention. In addition, this step is performed under conditions and in an environment that allow specific antigen-antibody binding. The expert is familiar with suitable conditions. Preferably, these conditions include a liquid environment (optionally also solid substrate materials) and/or bringing into contact at a temperature of >0° C. to <60° C. Bringing into contact should preferably be performed over a period that allows the formation of a specific antigen-antibody binding between the complex used in accordance with the invention and any specific antibodies for the complex contained in the sample of microbial transglutaminase and gliadin or their immunologically active parts.

In a subsequent step of the usage in accordance with the invention, an antibody is identified that is specifically bound to the complex of microbial transglutaminase and gliadin peptides or their immunologically active parts. The proof of the antibody specifically bound to the complex used in accordance with the invention can, for example, be provided by such components of the sample that are not bound to the complex of microbial transglutaminase and gliadin or the immunologically active parts of this complex that are removed after bringing into contact, e.g. by one or more washing, cleaning or isolation steps. A specific proof of the presence antibodies by means of standard methods which are familiar to the expert can then be performed. The proof may thereby be obtained in one or more steps. The agents used for the specific identification of antibodies may, for example, themselves be antibodies. Identification can then, for example, be performed via a colour reaction, which is directly or indirectly mediated or triggered by the agents for identifying the presence of antibodies. For example, antibodies for the identification of specific antibodies can be bound to functional groups or molecules (e.g. enzymes), which are able to trigger or mediate a colour reaction under certain conditions.

When used in accordance with the invention, the complex of microbial transglutaminase and gliadin or their immunologically active parts can be immobilised on a substrate during one, several or all steps. Immobilisation in this regard is understood to be any coupling, binding or other association between complex and substrate with the effect that complex and substrate cannot move independently of each other. Molecules and/or surfaces, for example, can be used as substrates whose form is such that they can bind to the complex reversibly or irreversibly. In addition, substrates and/or gliadins used in accordance with the invention and/or complexes used in accordance with the invention may present functional groups that support and/or enable binding between gliadins and/or complexes and substrates used in accordance with the invention. For example, BSA or surfaces are mentioned as substrate molecules, as they are offered by microparticles, nanoparticles or magnetic beads or surfaces of selected membranes, polymers (e.g. polystyrenes) or microtitre plates or test strips containing such surfaces. The expert is familiar with suitable substrates and options for binding protein complexes and substrates.

In particular, the procedure in accordance with the invention can be performed as an immunoassay procedure, suitable immunoassay procedures are described in "Labor und Diagnose," p. 756 ff. (ISBN 3980521567)

The procedure in accordance with the invention can preferably be performed as an ELISA procedure (ELISA=enzyme-linked immunosorbent assay), suitable ELISA techniques are for example described in "Labor und Diagnose," p. 1470 ff. (ISBN 3980521567). To this end, a sample can be brought into contact with a complex used in accordance with the invention that is immobilised on a substrate with, if necessary, the unbound components being partially or basically removed, then an antibody bound or bindable to a functional group is used as proof of the presence of sample antibody bound to the complex used in accordance with the invention. Proof is generally provided by means of a visually detectable reaction.

The antibody for proof may, for example, be specific for antibodies of a certain organism or a certain origin and/or for a certain form of the antibody, preferably for a certain isotype e.g. antibodies of the types IgA, IgM, IgE and/or IgG, particularly preferred for human IgA, IgM, IgE and/or human IgG.

Usage in accordance with the invention can, however, also be performed in other formats, thus, for example, as a RIA (radio-immunoassay), as an immunoassay (e.g. so-called lineblots or ELISAs) or in fluid-based procedures such as HTRF (homogeneous time resolved fluorescence). Usage in accordance with the invention can also take the form of so-called multiplex assays (assays with other biomarkers) in combination in the above-mentioned technical procedures.

This invention is suitable for demonstrating the presence of antibodies against a complex used in accordance with the invention, in particular for demonstrating the presence of antibodies of types IgA, IgG, IgM and/or IgE, preferably for demonstrating the presence of antibodies of human origin.

Usage in accordance with the invention can be applied for diagnosis, in particular for serological diagnosis, preferably for the diagnosis of coeliac disease and/or endemic sprue and/or tropical sprue and/or in the early detection of general gluten intolerance and/or dermatitis herpetiformis.

This invention also includes a kit for the assay or diagnosis and/or therapy control of coeliac disease or sprue as well as of gluten sensitivity, whereby the kit contains a microbial transglutaminase or its immunologically reactive parts or analogues, which are present in a complex with gliadin or its immunologically reactive parts or analogues. In addition, the kit may contain instructions on using the kit and/or on the procedure for using the kit in accordance with the invention.

The kit is preferably in the form of an ELISA or in particular a strip test. This means that the kit used in accordance with the invention includes the complex used in accordance with the invention and, if necessary, other components for the procedure for usage in accordance with the invention in a form that is suitable for the ELISA and/or strip test format. In particular, the kit may include the complex used in accordance with the invention bound to a test strip.

The kit used in accordance with the invention may, if necessary, contain other components for the procedure for usage in accordance with the invention. Such components may, for example, include reaction vessels, filters, solutions, protein-modified enzymes and/or other agents. In particular, the kit in accordance with the invention may contain agents for demonstrating the presence of antibodies, preferably of human antibodies of the IgA, IgM, IgE and/or of the IgG type.

In particular, the kit used in accordance with the invention is suitable for use in diagnosis, preferably in serological diagnosis, with particular preference given to the diagnosis of coeliac disease, sprue, dermatitis herpetiformis and/or gluten sensitivity.

The kit used in accordance with the invention, if necessary, may contain other agents for the procedure for usage in accordance with the invention and/or for classification of the coeliac disease or sprue into specific sub-groups (see above, e.g. silent, latent or established coeliac disease). Such agents may, for example, contain tTg antibodies, tTg/gliadin peptide complex antibodies, DGP antibodies, gliadin antibodies etc.

EXAMPLES

Amino Acid Sequence Alignments

The intention is to demonstrate that the microbial transglutaminase (mTG) from *Streptomyces mobaraensis* and the human transglutaminase (TG2) have few similarities at the sequence level.

For this purpose, the sequences Q5UCB5 (mTG) (SEQ ID NO: 1) and P21980 (SEQ ID NO: 3) available in the Uniprot database were compared. A sequence comparison was performed by means of the "pairwise alignment tool" EMBOSS available on the internet. The algorithms "needle" or "stretcher" were used.

As can be seen from FIG. 1A, FIG. 1B, FIG. 2A and FIG. 2B, there is almost no homology between the sequences used, regardless of which algorithm is used. When the stretcher algorithm is used, the paired alignment between microbial transglutaminase from *Streptomyces mobaraensis* and human tissue transglutaminase has a similarity of only 23.6% and an identity of 14.3%, and when the "needle" algorithm is used, a similarity of only 15.3% and an identity of 9.2%.

Competitive Assays

Competitive assays determine whether there is a relationship between the formed complex of human tissue transglutaminase with gliadin and the complex used in accordance with the invention. To this end, patient serums that contain the antibodies against the complex of tissue transglutaminase and gliadin mixed with the individual components and with the complex, formed in accordance with the invention, of microbial transglutaminase and gliadin and deposited on a microtitre plate coated with a complex of tissue transglutaminase and gliadin. Via the intensity of a colour reaction, it can now be determined how strongly each component contributes to the test result, i.e. which reactive fraction of the antibodies binds to the respective components. If the antibodies not only bind to the complex of human tissue transglutaminase and gliadin, but also to the other competitors, these antibodies are captured (and can therefore no longer bind to the microtitre plate) and the colour reaction is less in comparison to the reference value. In order to obtain a reference value, the patient serum is directly applied to the plate coated with the complex of human tissue transglutaminase and gliadin.

In order to perform the competitive assay, an AESKUKLISA tTg New Generation Kit from AESKU.Diagnostics was used, which is suitable for a separate quantitative and qualitative assay of IgA and/or IgG antibodies, targeted at a complex of tissue transglutaminase and gliadin, in human serums.

Concentrations of Individual Components:

The components mTG, DGP, tTG and gliadin were used in concentrations of 0; 0.125; 0.25; 0.5; 0.75 and 1.0 µg/ml (duplicate assay of the respective concentration was performed).

Each serum was incubated with the respective competitor and then measured in the ELISA standard as per the manufacturer's instructions.

Serums Used:

Coeliac disease serums with the serum numbers 1011, 1020, 1038 and 1045 were used. The serums 1011 and 1038 were prediluted 1:10 with a blood donor serum and then once again prediluted 1:100 with a sample buffer.

The degree of competition was calculated in comparison to a reference value for each serum. The reference value was set to 100% and diagrams generated with the aid of Microsoft Office Excel.

Figure 3:
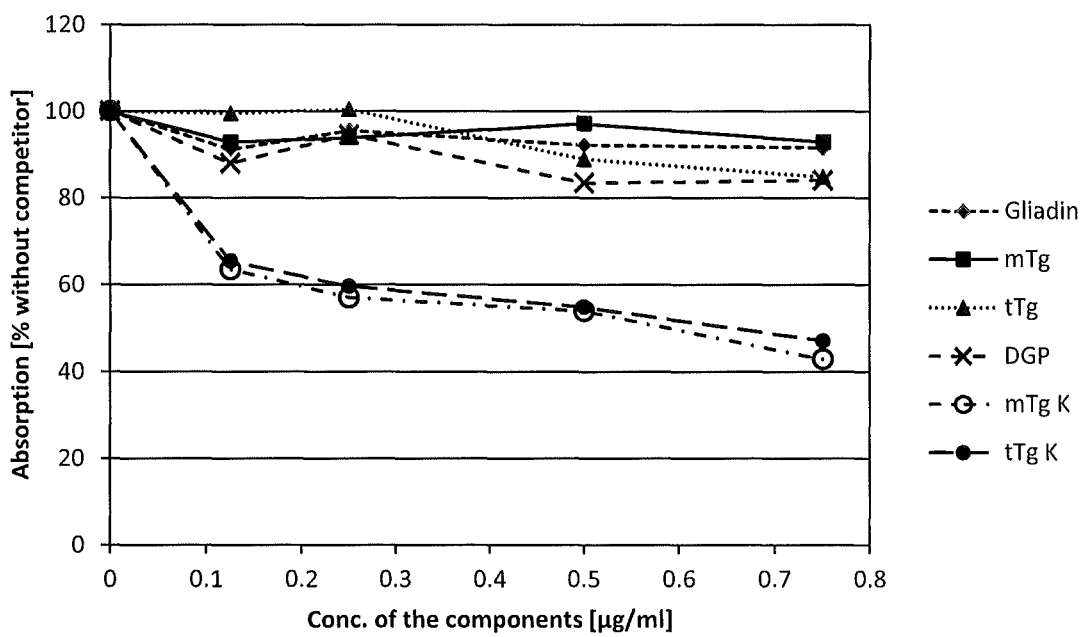
FIG. 3 shows the results of a competitive assay for serum 1011 (IgA) in the form of a diagram, whereby the absorption is presented in relation to the concentration of competitors. The individual competitors can be obtained from the diagram legend.
Figure 4:
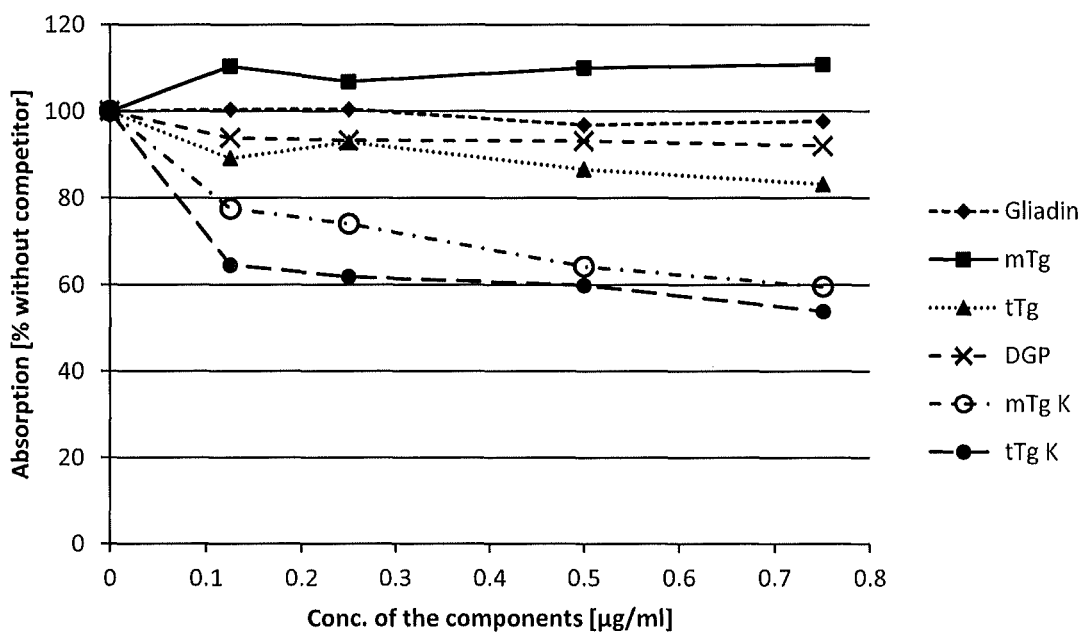
FIG. 4 shows the results of a competitive assay for serum 1038 (IgA) in the form of a diagram, whereby the absorption is presented in relation to the concentration of competitors. The individual competitors can be obtained from the diagram legend.
Figure 6:
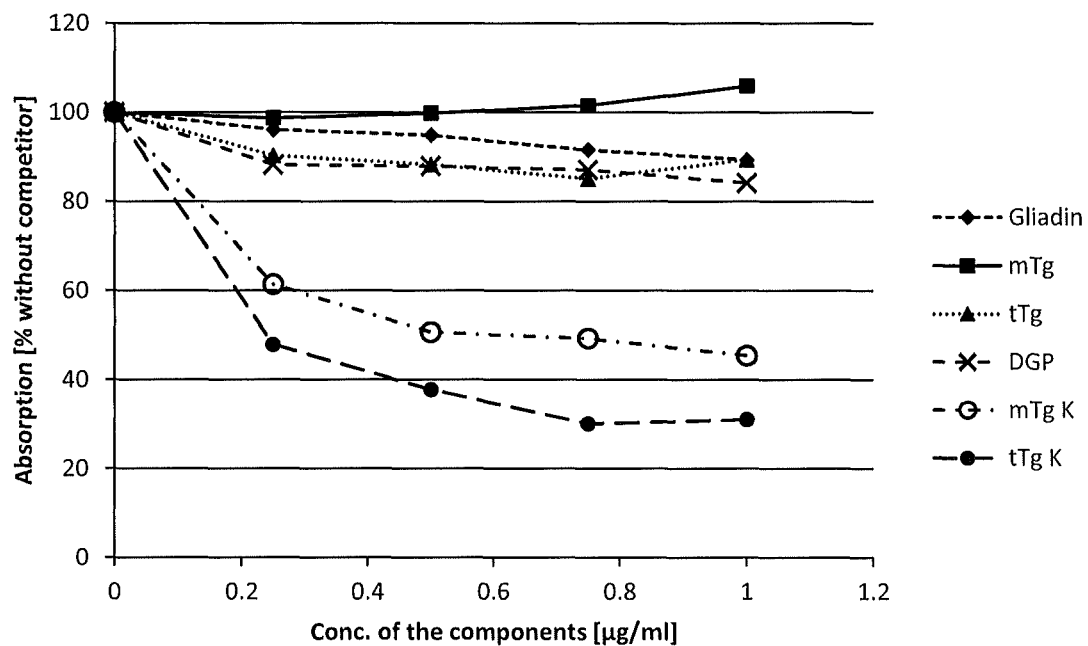
FIG. 6 shows the results of a competitive assay for serum 1038 (IgG) in the form of a diagram, whereby the absorption is presented in relation to the concentration of the competitors. The individual competitors can be obtained from the diagram legend.
Figure 7:
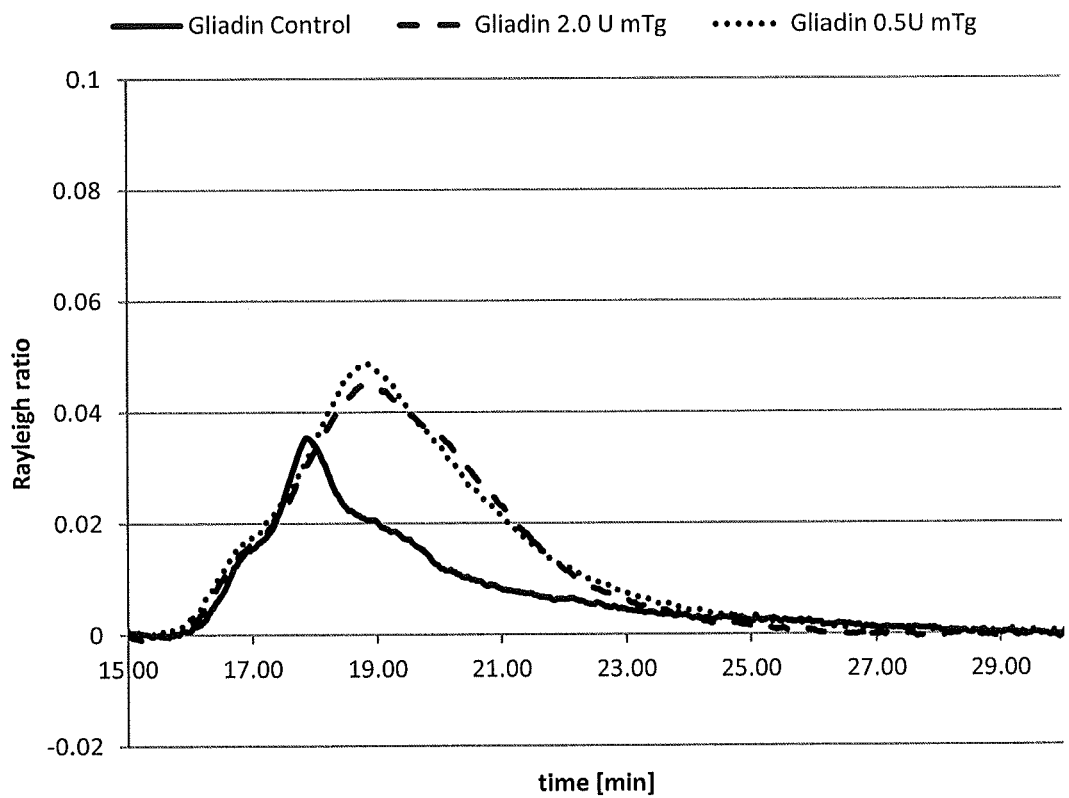
FIG. 7 shows the results, in the form of a diagram, of a measurement via AF4-MALS for the formation of complexes of gliadin and microbial transglutaminase, whereby the so-called "Rayleigh" ratio is presented in relation to the time. The individual components of the measurement can be obtained from the diagram legend.
Figure 8:
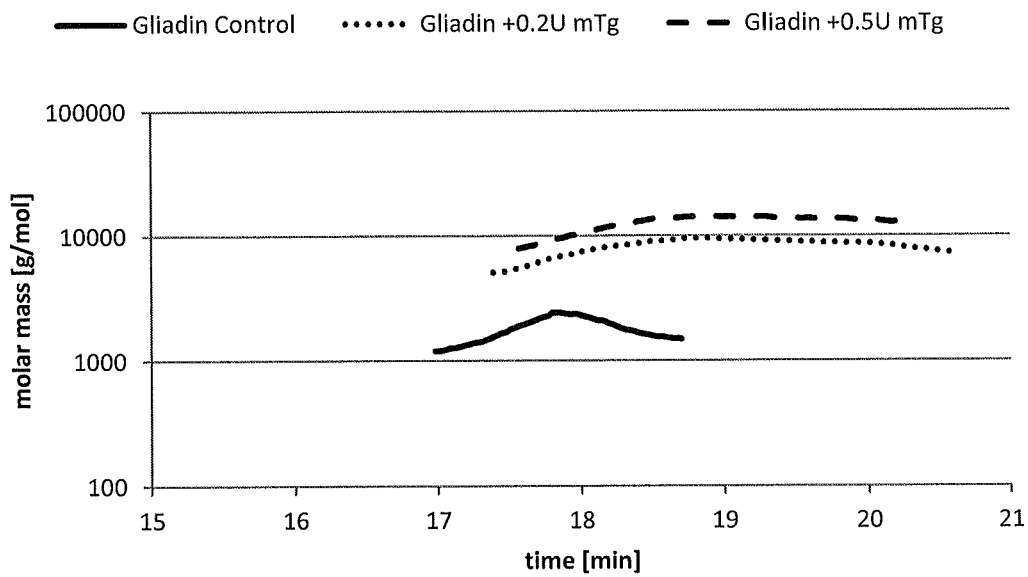
FIG. 8 shows the results, in the form of a diagram, of a measurement via AF4-MALS for the formation of complexes of gliadin and microbial transglutaminase, whereby the molar mass in g/mol is presented in relation to time. The individual components of the measurement can be obtained from the diagram legend.
Figure 9:
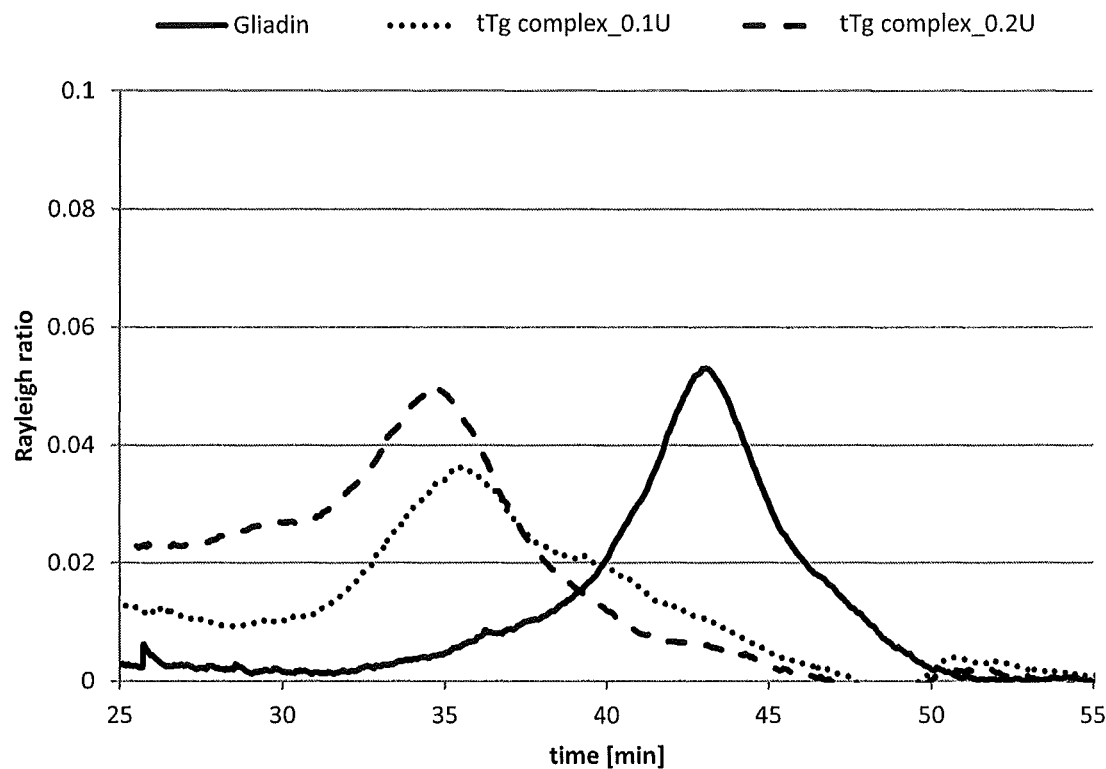
FIG. 9 shows the results, in the form of a diagram, of a measurement via SEC-MALS for the formation of complexes of gliadin and tissue transglutaminase, whereby the so-called "Rayleigh" ratio is presented in relation to time.

Results of the Competitive Assay IgA and IgG:

It is apparent that antibodies are absorbed by the individual components, see serums 1011 and 1038 (FIG. 3 and FIG. 4 for IgA and FIG. 5 and FIG. 6 for IgG). In all four cases, the addition of the components DGP, gliadin and mTg has hardly any influence on the colour intensity of the reaction, so that it may be assumed that the antibodies in the patient serums are exclusively directed against the complex used in accordance with the invention.

Measurements of the Formation of Complexes Via AF4/SEC MALS

The respective complexes were separated via a size exclusion chromatography (SEC) column or via asymmetrical flow field-flow fractionation AF4 and analysed via multi-angle light scattering (MALS).

The measurement using MALS enables a comparison of the mass distribution contained in a sample. With the aid of the MALS mass comparison, the conversion of the individual component gliadin with the respective transglutaminase (mTg or tTg) to a complex can be demonstrated.

Addition of mTg results in significantly higher masses in comparison to gliadin without mTg ELISA Analysis of Coeliac Disease Patient Serums The used coeliac disease serums (N=82) as well as 33 control serums (blood donor) were tested with the following AESKU kits and on self-coated plates.

The serums were tested for IgA and for IgG antibodies against the individual components or complexes.

AESKU kits:
  AESKULISA Glia
  AESKULISA DGP
  AESKULISA tTg
  AESKULISA tTg New Generation
Self-coated plates:
  Microbial transglutaminase
  Gliadin in water
  Gliadin with microbial transglutaminase
  Purified mTg—gliadin complex The results of the ELISA are summarised in Table 1. The concentration of the protein solutions were determined by means of the OD at 280 nm (assumption: 1 OD=1 µg/ml).

TABLE 1

Excerpts from the ROC analysis.

| Marker | AUC | Sensitivity | Specificity |
|---|---|---|---|
| AESKULISA tTg-G New Generation | 0.95 +/− 0.02 | 0.87 +/− 0.04 | 0.93 +/− 0.03 |
| AESKULISA GliaG | 0.671 +/− 0.042 | 0.65 +/− 0.06 | 0.89 +/− 0.04 |
| mTg-GP complex IgG | 0.89 +/− 0.03 | 0.91 +/− 0.03 | 1.00 +/− 0.00 |
| tTg-IgG ELISA | 0.81 +/− 0.04 | 0.6 +/− 0.06 | 0.94 +/− 0.03 |
| mTg-IgG ELISA | | cannot be determined | |
| AESKULISA DGP IgG | 0.73 +/− 0.04 | 0.58 +/− 0.06 | 0.79 +/− 0.05 |
| AESKULISA tTg A New Generation | 0.95 +/− 0.02 | 0.89 +/− 0.04 | 0.93 +/− 0.03 |
| AESKULISA Glia A | 0.77 +/− 0.04 | 0.67 +/− 0.06 | 0.81 +/− 0.04 |
| mTg complex IgA | 0.90 +/− 0.03 | 0.69 +/− 0.054 | 1.00 +/− 0.00 |
| tTg-IgA ELISA | 0.87 +/− 0.03 | 0.62 +/− 0.06 | 1.00 +/− 0.00 |
| mTg-IgA ELISA | | cannot be determined | |
| AESKULISA DGP IgA | 0.68 +/− 0.04 | 0.41 +/− 0.06 | 0.96 +/− 0.02 |

Since no transformation into other units is possible for mTg ELISAs (no established tests), this analysis is based on the optical densities of the assays, whereby the sensitivity/specificity ratio has been optimised so that its sum is maximised (Youden index).

Due to the selection bias, these values deviate from those of a clinical study.

As Table 1 shows, the mTg complex ELISAs perform differently to the other parameters and also differently to the tTG-gliadin complex ELISAs. It should be noted, that it is not possible to distinguish from pure mTg with the antibodies. It should be noted that although the results of the tTG2-gliadin complex ELISAs were significantly better than for the mTg-gliadin complex ELISAs, these were in turn better than the remaining ELISAs—although the patients hardly respond to the mTg directly. As previously explained, an epitope similarity between tTG2-gliadin complexes and mTg-gliadin complexes is to be assumed—however, not necessarily epitope equivalence.

If the complex used in accordance with the invention produces the first immunopotent epitope for a coeliac disorder, then molecular epitope mimicry can result in the patient's immune system recruiting antibodies against the body's own tissue transglutaminase in the complex with gliadin and subsequently—as a consequence of secondary molecular epitope mimicry—against epitopes which also recruit tissue transglutaminase, gliadin, gliadin peptides or deamidated derivatives (DGPs=deamidated gliadin peptides). Coeliac disease patients do not appear to form their antibody titres against certain epitopes at any time, but it seems that transient transitions from one of the described epitopes is formed which perfectly characterises the progression of the disease while retaining "residual titres", since a gluten-free diet can result in a lower titre of the established antibodies.

In order to demonstrate the above, a multiple Wilcoxon-Mann-Whitney test (also U test) was conducted as a rank sum test on an existing serum panel (75 independent coeliac disease patient samples of various nationalities) and the P values presented as a measure of the differences of the rank distribution. Here, the P value—in accordance with the Manhattan plot—is logarithmised and its sign inverted (the more pronounced the rank sum difference of the parameter pairs, the higher the column), whereby the horizontal column corresponds to the Bonferroni significance threshold, as the most conservative possible correction for multiple testing.

In accordance with the above facts, it can be assumed that analogue epitope pairs (e.g. anti-gliadin antibodies vs. DGP antibodies or anti-mTgase-gliadin peptide complex antibodies vs. anti-human tissue transglutaminase complex antibodies) will exhibit more even rank sums (smaller P-value columns) than epitopes, whose titre magnitudes correlate with the progression of the disease (e.g. anti-mTgase-gliadin peptide complex antibodies vs. anti-gliadin antibodies).

Detection of these antibodies enables coeliac disease or sprue patients to be identified, who cannot be identified using one or more other serological diagnostic tests for coeliac disease or sprue. This means that with usage in accordance with the invention, those patients who were previously classified as false negative can be identified. In our panel of 75 coeliac-positive serums, this concerned 8 serums with an anti-tTg-gliadin complex antibody test, 25 serums in the anti-gliadin antibody test, 44 serums in the anti-DGP antibody test and 28 serums in the anti-tTg antibody test in relation to the IgA antibodies. The diagnostic gap that can thus be closed is therefore highly significant (P-value of $7.4*10e-8$ in a Cochrane-Armitage trend test on the trend of the complex used in accordance with the invention). With the introduction of the kit referred to in the claim, an even greater gap can be closed, since the analysed serum panel is subject to a selective bias, which leans towards patients who had in any case been identified as positive.

The discovery of the complex used in accordance with the invention is all the more surprising since virtually no homology exists between microbial transglutaminase and tissue transglutaminase.

Procedure for the Presymptomatic Diagnosis of Coeliac Disease and Gluten Sensitivity

SUMMARY

The invention relates to the use of an immunologically reactive microbial transglutaminase or its immunologically reactive parts or analogues, which are present in a complex with gliadin or its immunologically reactive parts or analogues, for the diagnosis and/or therapy control of coeliac disease or sprue as well as gluten sensitivity, and a kit for determining the diagnosis and/or therapy control of coeliac disease or sprue as well as of gluten sensitivity, by means of the previously mentioned complex.

We claim:

1. A method for at least one of diagnosis and therapeutic control of at least one of coeliac disease, sprue, and gluten sensitivity, comprising:
   administering to a patient in need of diagnosis or therapeutic control of at least one of coeliac disease, sprue, and gluten sensitivity (a) a microbial transglutaminase, and (b) a gliadin;
   wherein (a) and (b) are cross-linked; and wherein (a) comprises the amino acid sequence of SEQ ID NO: 1, and (b) comprises the amino acid sequence of SEQ ID NO: 2.

2. The method of claim 1, further comprising detecting antibodies wherein the antibodies are selected from the group consisting of human IgA, IgG, IgM and IgE antibodies.

3. A kit for at least one of diagnosis and therapy control of at least one of coeliac disease, sprue, and gluten sensitivity, comprising:
   (a) a microbial transglutaminase, and
   (b) a gliadin;
   wherein (a) and (b) are cross-linked, wherein (a) comprises the amino acid sequence of SEQ ID NO: 1, and (b) comprises the amino acid sequence of SEQ ID NO: 2.

4. The kit of claim 3, further comprising agents which bind to IgA, IgG, IgM, and/or IgE antibodies.

5. The kit of claim 3, further comprising one or more antibodies selected from the list consisting of a tTg antibody, a tTg/gliadin peptide complex antibody, a DGP antibody, and a gliadin antibody.

6. The kit of claim 3, further comprising at least one antibody selected from the group consisting of isolated monoclonal antibodies, isolated polyclonal antibodies, and isolated recombinant antibodies, wherein said antibody is capable of binding to (a) and/or (b).

7. The kit of claim 3, for diagnosis and/or therapy control of coeliac disease.

8. The kit of claim 3, for diagnosis and/or therapy control of sprue.

9. The kit of claim 3, for diagnosis and/or therapy control of gluten sensitivity.

* * * * *

SEQUENCE LISTING

```
<160> NUMBER OF SEQ ID NOS: 3

<210> SEQ ID NO 1
<211> LENGTH: 410
<212> TYPE: PRT
<213> ORGANISM: Streptomyces mobaraensis

<400> SEQUENCE: 1

Met Ser Gln Arg Gly Arg Thr Leu Val Phe Ala Ala Leu Gly Ala Val
1               5                   10                  15

Met Cys Thr Thr Ala Leu Met Pro Ser Ala Gly Ala Ala Thr Gly Ser
                20                  25                  30

Gly Ser Gly Ser Gly Thr Gly Glu Glu Lys Arg Ser Tyr Ala Glu Thr
            35                  40                  45

His Arg Leu Thr Ala Asp Asp Val Asp Asp Ile Asn Ala Leu Asn Glu
        50                  55                  60

Ser Ala Pro Ala Ala Ser Ser Ala Gly Pro Ser Phe Arg Ala Pro Asp
65                  70                  75                  80

Ser Asp Glu Arg Val Thr Pro Pro Ala Glu Pro Leu Asp Arg Met Pro
                85                  90                  95
```

```
Asp Pro Tyr Arg Pro Ser Tyr Gly Arg Ala Glu Thr Ile Val Asn Asn
                100                 105                 110

Tyr Ile Arg Lys Trp Gln Gln Val Tyr Ser His Arg Asp Gly Arg Lys
            115                 120                 125

Gln Gln Met Thr Glu Glu Gln Arg Glu Trp Leu Ser Tyr Gly Cys Val
        130                 135                 140

Gly Val Thr Trp Val Asn Ser Gly Gln Tyr Pro Thr Asn Arg Leu Ala
145                 150                 155                 160

Phe Ala Phe Phe Asp Glu Asp Lys Tyr Lys Asn Glu Leu Lys Asn Gly
                165                 170                 175

Arg Pro Arg Ser Gly Glu Thr Arg Ala Glu Phe Glu Gly Arg Val Ala
            180                 185                 190

Lys Asp Ser Phe Asp Glu Ala Lys Gly Phe Gln Arg Ala Arg Asp Val
        195                 200                 205

Ala Ser Val Met Asn Lys Ala Leu Glu Asn Ala His Asp Glu Gly Ala
210                 215                 220

Tyr Leu Asp Asn Leu Lys Lys Glu Leu Ala Asn Gly Asn Asp Ala Leu
225                 230                 235                 240

Arg Asn Glu Asp Ala Arg Ser Pro Phe Tyr Ser Ala Leu Arg Asn Thr
                245                 250                 255

Pro Ser Phe Lys Asp Arg Asn Gly Asn His Asp Pro Ser Lys Met
            260                 265                 270

Lys Ala Val Ile Tyr Ser Lys His Phe Trp Ser Gly Gln Asp Arg Ser
        275                 280                 285

Gly Ser Ser Asp Lys Arg Lys Tyr Gly Asp Pro Glu Ala Phe Arg Pro
290                 295                 300

Asp Arg Gly Thr Gly Leu Val Asp Met Ser Arg Asp Arg Asn Ile Pro
305                 310                 315                 320

Arg Ser Pro Thr Ser Pro Gly Glu Ser Phe Val Asn Phe Asp Tyr Gly
                325                 330                 335

Trp Phe Gly Ala Gln Thr Glu Ala Asp Ala Asp Lys Thr Val Trp Thr
            340                 345                 350

His Gly Asn His Tyr His Ala Pro Asn Gly Ser Leu Gly Ala Met His
        355                 360                 365

Val Tyr Glu Ser Lys Phe Arg Asn Trp Ser Asp Gly Tyr Ser Asp Phe
370                 375                 380

Asp Arg Gly Ala Tyr Val Val Thr Phe Val Pro Lys Ser Trp Asn Thr
385                 390                 395                 400

Ala Pro Asp Lys Val Lys Gln Gly Trp Pro
                405                 410

<210> SEQ ID NO 2
<211> LENGTH: 286
<212> TYPE: PRT
<213> ORGANISM: Triticum aestivum

<400> SEQUENCE: 2

Met Lys Thr Phe Leu Ile Leu Val Leu Leu Ala Ile Val Ala Thr Thr
1               5                   10                  15

Ala Thr Thr Ala Val Arg Phe Pro Val Pro Gln Leu Gln Pro Gln Asn
            20                  25                  30

Pro Ser Gln Gln Gln Pro Gln Glu Gln Val Pro Leu Val Gln Gln Gln
        35                  40                  45

Gln Phe Leu Gly Gln Gln Gln Pro Phe Pro Pro Gln Gln Pro Tyr Pro
50                  55                  60
```

-continued

```
Gln Pro Gln Pro Phe Pro Ser Gln Leu Pro Tyr Leu Gln Leu Gln Pro
 65                  70                  75                  80

Phe Pro Gln Pro Gln Leu Pro Tyr Ser Gln Pro Gln Pro Phe Arg Pro
                 85                  90                  95

Gln Gln Pro Tyr Pro Gln Pro Gln Pro Gln Tyr Ser Gln Pro Gln Gln
                100                 105                 110

Pro Ile Ser Gln Gln Gln Gln Gln Gln Gln Gln Gln Gln Gln Gln Gln
            115                 120                 125

Gln Gln Gln Gln Gln Ile Leu Gln Gln Ile Leu Gln Gln Gln Leu Ile
130                 135                 140

Pro Cys Met Asp Val Val Leu Gln His Asn Ile Ala His Gly Arg
145                 150                 155                 160

Ser Gln Val Leu Gln Gln Ser Thr Tyr Gln Leu Leu Gln Glu Leu Cys
                165                 170                 175

Cys Gln His Leu Trp Gln Ile Pro Glu Gln Ser Gln Cys Gln Ala Ile
            180                 185                 190

His Asn Val Val His Ala Ile Ile Leu His Gln Gln Lys Gln Gln
        195                 200                 205

Gln Gln Pro Ser Ser Gln Val Ser Phe Gln Gln Pro Leu Gln Gln Tyr
210                 215                 220

Pro Leu Gly Gln Gly Ser Phe Arg Pro Ser Gln Gln Asn Pro Gln Ala
225                 230                 235                 240

Gln Gly Ser Val Gln Pro Gln Leu Pro Gln Phe Glu Glu Ile Arg
            245                 250                 255

Asn Leu Ala Leu Gln Thr Leu Pro Ala Met Cys Asn Val Tyr Ile Pro
                260                 265                 270

Pro Tyr Cys Thr Ile Ala Pro Phe Gly Ile Phe Gly Thr Asn
            275                 280                 285
```

<210> SEQ ID NO 3
<211> LENGTH: 687
<212> TYPE: PRT
<213> ORGANISM: Homo sapiens

<400> SEQUENCE: 3

```
Met Ala Glu Glu Leu Val Leu Glu Arg Cys Asp Leu Glu Leu Glu Thr
 1               5                  10                  15

Asn Gly Arg Asp His His Thr Ala Asp Leu Cys Arg Glu Lys Leu Val
                 20                  25                  30

Val Arg Arg Gly Gln Pro Phe Trp Leu Thr Leu His Phe Glu Gly Arg
             35                  40                  45

Asn Tyr Glu Ala Ser Val Asp Ser Leu Thr Phe Ser Val Val Thr Gly
         50                  55                  60

Pro Ala Pro Ser Gln Glu Ala Gly Thr Lys Ala Arg Phe Pro Leu Arg
 65                  70                  75                  80

Asp Ala Val Glu Glu Gly Asp Trp Thr Ala Thr Val Val Asp Gln Gln
                 85                  90                  95

Asp Cys Thr Leu Ser Leu Gln Leu Thr Thr Pro Ala Asn Ala Pro Ile
                100                 105                 110

Gly Leu Tyr Arg Leu Ser Leu Glu Ala Ser Thr Gly Tyr Gln Gly Ser
            115                 120                 125

Ser Phe Val Leu Gly His Phe Ile Leu Leu Phe Asn Ala Trp Cys Pro
130                 135                 140

Ala Asp Ala Val Tyr Leu Asp Ser Glu Glu Glu Arg Gln Glu Tyr Val
```

-continued

```
            145                 150                 155                 160
Leu Thr Gln Gln Gly Phe Ile Tyr Gln Gly Ser Ala Lys Phe Ile Lys
                    165                 170                 175
Asn Ile Pro Trp Asn Phe Gly Gln Phe Glu Asp Gly Ile Leu Asp Ile
                    180                 185                 190
Cys Leu Ile Leu Leu Asp Val Asn Pro Lys Phe Leu Lys Asn Ala Gly
                    195                 200                 205
Arg Asp Cys Ser Arg Arg Ser Ser Pro Val Tyr Val Gly Arg Val Val
        210                 215                 220
Ser Gly Met Val Asn Cys Asn Asp Asp Gln Gly Val Leu Leu Gly Arg
225                 230                 235                 240
Trp Asp Asn Asn Tyr Gly Asp Gly Val Ser Pro Met Ser Trp Ile Gly
                    245                 250                 255
Ser Val Asp Ile Leu Arg Arg Trp Lys Asn His Gly Cys Gln Arg Val
                260                 265                 270
Lys Tyr Gly Gln Cys Trp Val Phe Ala Ala Val Ala Cys Thr Val Leu
            275                 280                 285
Arg Cys Leu Gly Ile Pro Thr Arg Val Val Thr Asn Tyr Asn Ser Ala
        290                 295                 300
His Asp Gln Asn Ser Asn Leu Leu Ile Glu Tyr Phe Arg Asn Glu Phe
305                 310                 315                 320
Gly Glu Ile Gln Gly Asp Lys Ser Glu Met Ile Trp Asn Phe His Cys
                    325                 330                 335
Trp Val Glu Ser Trp Met Thr Arg Pro Asp Leu Gln Pro Gly Tyr Glu
                340                 345                 350
Gly Trp Gln Ala Leu Asp Pro Thr Pro Gln Glu Lys Ser Glu Gly Thr
            355                 360                 365
Tyr Cys Cys Gly Pro Val Pro Val Arg Ala Ile Lys Glu Gly Asp Leu
        370                 375                 380
Ser Thr Lys Tyr Asp Ala Pro Phe Val Phe Ala Glu Val Asn Ala Asp
385                 390                 395                 400
Val Val Asp Trp Ile Gln Gln Asp Asp Gly Ser Val His Lys Ser Ile
                    405                 410                 415
Asn Arg Ser Leu Ile Val Gly Leu Lys Ile Ser Thr Lys Ser Val Gly
                420                 425                 430
Arg Asp Glu Arg Glu Asp Ile Thr His Thr Tyr Lys Tyr Pro Glu Gly
            435                 440                 445
Ser Ser Glu Glu Arg Glu Ala Phe Thr Arg Ala Asn His Leu Asn Lys
        450                 455                 460
Leu Ala Glu Lys Glu Glu Thr Gly Met Ala Met Arg Ile Arg Val Gly
465                 470                 475                 480
Gln Ser Met Asn Met Gly Ser Asp Phe Asp Val Phe Ala His Ile Thr
                    485                 490                 495
Asn Asn Thr Ala Glu Glu Tyr Val Cys Arg Leu Leu Leu Cys Ala Arg
                500                 505                 510
Thr Val Ser Tyr Asn Gly Ile Leu Gly Pro Glu Cys Gly Thr Lys Tyr
            515                 520                 525
Leu Leu Asn Leu Asn Leu Glu Pro Phe Ser Glu Lys Ser Val Pro Leu
        530                 535                 540
Cys Ile Leu Tyr Glu Lys Tyr Arg Asp Cys Leu Thr Glu Ser Asn Leu
545                 550                 555                 560
Ile Lys Val Arg Ala Leu Leu Val Glu Pro Val Ile Asn Ser Tyr Leu
                    565                 570                 575
```

```
Leu Ala Glu Arg Asp Leu Tyr Leu Glu Asn Pro Glu Ile Lys Ile Arg
            580             585             590

Ile Leu Gly Glu Pro Lys Gln Lys Arg Lys Leu Val Ala Glu Val Ser
        595             600             605

Leu Gln Asn Pro Leu Pro Val Ala Leu Glu Gly Cys Thr Phe Thr Val
    610             615             620

Glu Gly Ala Gly Leu Thr Glu Glu Gln Lys Thr Val Glu Ile Pro Asp
625             630             635             640

Pro Val Glu Ala Gly Glu Val Lys Val Arg Met Asp Leu Leu Pro
            645             650             655

Leu His Met Gly Leu His Lys Leu Val Val Asn Phe Glu Ser Asp Lys
            660             665             670

Leu Lys Ala Val Lys Gly Phe Arg Asn Val Ile Ile Gly Pro Ala
            675             680             685
```